(12) United States Patent
Philippe et al.

(10) Patent No.: US 11,424,009 B2
(45) Date of Patent: Aug. 23, 2022

(54) SYSTEM FOR ANALYSING GENOMIC DATA COMPRISING A PLURALITY OF APPLICATION NODES AND A KNOWLEDGE DATABASE

(71) Applicants: AXLR, SATT DU LANGUEDOC ROUSSILLON, Montpellier (FR); UNIVERSITE DE MONTPELLIER, Montpellier (FR); INSTITUT NATIONAL DE LA SANTE ET DE LA RECHERCHE MEDICALE, Paris (FR); SEQONE, Montpellier (FR)

(72) Inventors: Nicolas Philippe, Clermont l'Hérault (FR); Guillaume Buwalda, Levallois (FR)

(73) Assignee: SEQONE, Montpellier (FR)

( * ) Notice: Subject to any disclaimer, the term of this patent is extended or adjusted under 35 U.S.C. 154(b) by 1096 days.

(21) Appl. No.: 16/061,560

(22) PCT Filed: Dec. 16, 2016

(86) PCT No.: PCT/EP2016/081575
§ 371 (c)(1),
(2) Date: Jun. 12, 2018

(87) PCT Pub. No.: WO2017/103202
PCT Pub. Date: Jun. 22, 2017

(65) Prior Publication Data
US 2019/0180847 A1    Jun. 13, 2019

(30) Foreign Application Priority Data
Dec. 18, 2015  (FR) ..................................... 1562828

(51) Int. Cl.
*G16B 50/30*  (2019.01)
*G16B 50/00*  (2019.01)
*G16B 20/00*  (2019.01)
*G06N 5/00*   (2006.01)

(52) U.S. Cl.
CPC ............... *G16B 50/30* (2019.02); *G06N 5/00* (2013.01); *G16B 20/00* (2019.02); *G16B 50/00* (2019.02)

(58) Field of Classification Search
None
See application file for complete search history.

(56) References Cited

U.S. PATENT DOCUMENTS

2010/0281401 A1   11/2010   Tebbs et al.
2015/0310228 A1   10/2015   Benz et al.

OTHER PUBLICATIONS

International Search Report as issued in International Patent Application No. PCT/EP2016/081575, dated Apr. 13, 2017.

*Primary Examiner* — G Steven Vanni
(74) *Attorney, Agent, or Firm* — Pillsbury Winthrop Shaw Pittman LLP

(57) ABSTRACT

A genomic data analysis architecture includes a plurality of application nodes, each application node including a calculation system including at least one calculation node, the calculation system being constructed and arranged so as to carry out genomic calculations, a human-machine interface constructed and arranged so as to communicate with the calculation system, and a knowledge base access interface, and including a knowledge base constructed and arranged so as to communicate with the plurality of application nodes. The knowledge base contains genomic data.

8 Claims, 1 Drawing Sheet

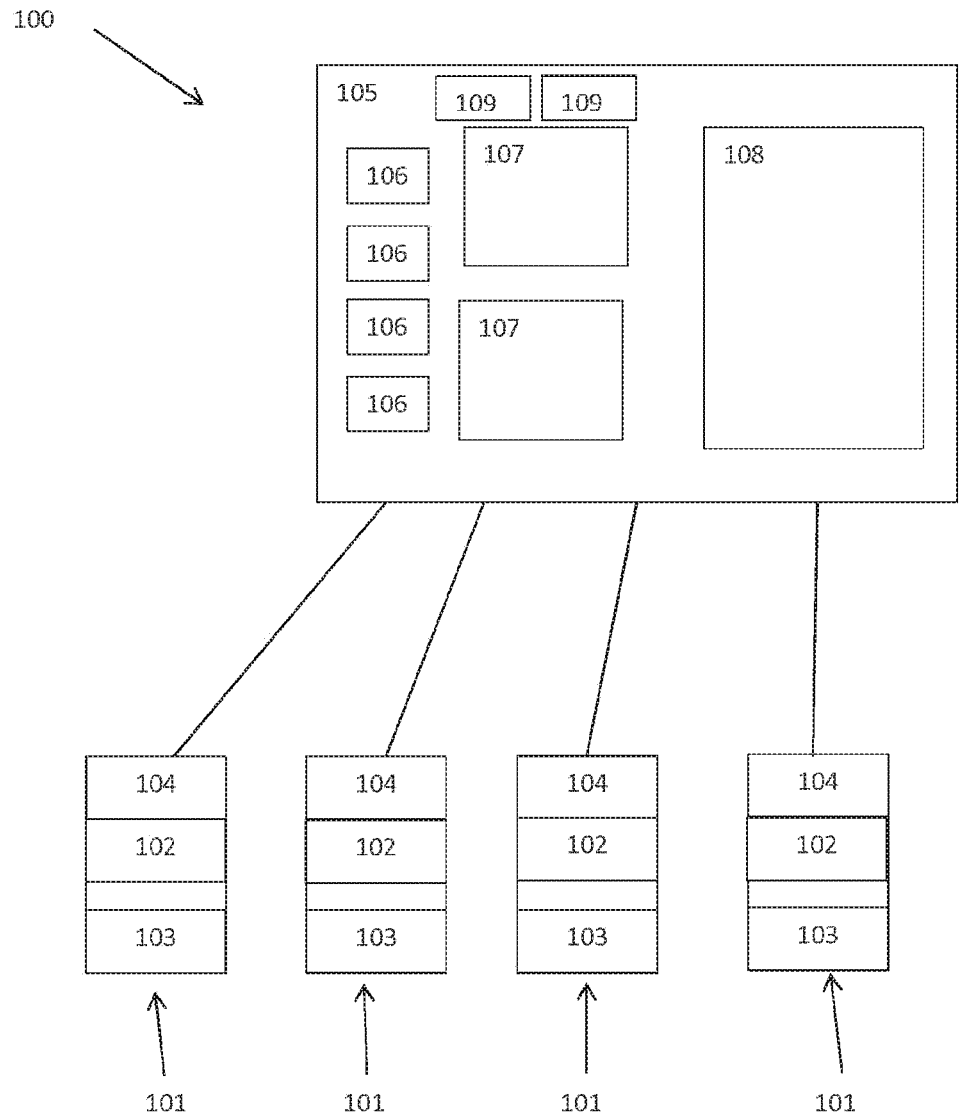

SYSTEM FOR ANALYSING GENOMIC DATA COMPRISING A PLURALITY OF APPLICATION NODES AND A KNOWLEDGE DATABASE

CROSS-REFERENCE TO RELATED APPLICATIONS

This application is the U.S. National Stage of PCT/EP2016/081575, filed Dec. 16, 2016, which in turn claims priority to French patent application number 1562828 filed Dec. 18, 2015. The content of these applications are incorporated herein by reference in their entireties.

TECHNICAL FIELD OF THE INVENTION

One aspect of the invention relates to an architecture for analysing genomic data, such as short sequences of ribonucleic acid (RNA) or deoxyribonucleic acid (DNA).

TECHNOLOGICAL BACKGROUND OF THE INVENTION

DNA sequencers have appeared in the 1970-'s with the objective to digitise DNA of the cells of living organisms. These sequencers have in particular allowed sequencing of the first human genome during the 1990's. At that time, this sequencing has required more than 10 years of work and about 1 billion dollars. Recently, a major technological advance has resulted in the emergence of a new generation of high throughput sequencers (also known as new generation sequencing (NGS)), and has modified the landscape of cellular and molecular biology. The sequencing cost has become quite affordable and the dramatic increase in the production capacity of these sequencers allowed the sequencing of entire genomes in only a few days.

Today, this technological revolution drastically changes biology and medicine. In cancerology for example, it is now possible to sequence very quickly all the information contained in the cancer cells of a patient, in view of searching for molecular markers which will be used for diagnostic, prognostic, follow-up of the residual disease or response to the treatment. However, the sequencers have always been limited, and continue to be, because of the size of sequenced DNA fragments. The preparation of a sample consists in cutting it in short DNA strands (of a few hundred nucleotides only) such that a sequencer can very quickly produce, hundreds of millions of short DNA (or RNA) sequences, under a textual form: these are called reads. These reads wholly cover the starting genetic material (for example the genome or the transcriptome of an individual). But, the information they produce is cut into a puzzle of millions of completely disorganised reads and some of which contain errors produced upon sequencing or preparing the sample. In other words, the sequences produced by the NGSS are restrictive and do not lead to results which can be exploited simply.

Biologists and clinicians face a huge amount of data (Big Data) that are to be stored, sorted, structured and interpreted. However, no tool appropriate to the exploitation of these data is today provided to the biologists nor even to the clinicians.

GENERAL DESCRIPTION OF THE INVENTION

In this context, the present invention aims at providing an architecture for analysing genomic data enabling genomic data obtained by means of a high throughput sequencer to be efficiently exploited.

To that end, one aspect of the invention relates to an architecture for analysing genomic data including:
a plurality of applicative nodes, each of the applicative nodes including:
a calculation system including at least one calculation node, the calculation system being constructed and arranged to carry out genomic calculations,
a human-machine interface constructed and arranged to communicate with the calculation system,
an interface for accessing a knowledge base,
a knowledge base constructed and arranged to communicate with the plurality of applicative nodes, said knowledge base containing genomic data; and
a plurality of private spaces, each of the private spaces being constructed and arranged:
to contain metadata and results from a calculation carried out by the calculation system of an authenticated entity including 1 to n user(s), and
to be read only accessible to the users of the authenticated entity.

By virtue of the invention, a user can carry out, via a calculation system, calculations on genomic data contained for example in the knowledge base. The results of the calculations carried out can be stored in the knowledge base and be accessible to other users, which other users can for example enrich these results by comparing them with theirs.

This architecture thus forms a collaborative work environment for analyses of data from new high throughput sequencing technologies (NGS). This collaborative work environment enables accurate and interpreted genomic analyses of a pathology or a patient to be carried out, in connection with a biological and/or medical question, while offering a simplified access, which is completely independent, to complex results.

Further, it should be noted that the architecture relies on:
a multi-tenant system because several users can use a single calculation node of a single calculation system, and
a multi-instance system because a user can use several calculation nodes of a calculation system.

This hybrid architecture makes it possible to take the most of both systems and thus to ensure confidentiality of the most calculation resource consuming users.

According to different aspects of the invention, the architecture for analysing genomic data can also have one or more of the characteristics hereinafter, considered singly or according to all technically feasible combinations.

In a non-limiting implementation, the architecture includes a plurality of shared spaces, each of the shared spaces being constructed and arranged:
to contain metadata and results from collaborative calculations carried out by the calculation systems of an authenticated entity including 1 to n user(s), and
to be read only accessible to the users of the authenticated entities and benefiting from a consultation right to said space.

According to a non-limiting implementation, the architecture includes a common space, said common space being accessible to all the users of the authenticated entities of the architecture.

In a non-limiting implementation, the calculation system is constructed and arranged to classify short digital sequences of biological material.

In a non-limiting implementation, the calculation system is constructed and arranged to aggregate the short digital sequences of biological material of a same class.

In a non-limiting implementation, the calculation system is constructed and arranged to identify a biomarker sequence answering a biological question.

In a non-limiting implementation, the architecture includes a plurality of resources, said resources being formed by:
- a system for identifying an entity and elements it handles,
- a system for identifying a user,
- a system for identifying a calculation associated with at least one user and one entity,
- a system enabling calculations carried out to be correlated,
- a system for logically gathering identifiers of calculations associated with a user and an entity,
- a system enabling a piece of meta-information to be associated with data from the knowledge base.

In a non-limiting implementation, the knowledge base is formed by a data base ring.

In a non-limiting implementation, the interface for accessing the knowledge base is an API REST.

BRIEF DESCRIPTION OF THE FIGURE

Further characteristics and advantages of the invention will become more clearly apparent from the description given below, by way of indicating and no way limiting purposes, in reference to the appended FIG. 1 schematically illustrating an architecture for analysing genomic data in accordance with one aspect of the invention.

DETAILED DESCRIPTION OF AT LEAST ONE EMBODIMENT OF THE INVENTION

FIG. 1 illustrates an exemplary embodiment of an architecture 100 for analysing genomic data according to a non-limiting aspect of the invention.

This architecture 100 includes a plurality of applicative nodes 101. Each of the applicative nodes 101 includes a calculation system 102 including at least one calculation node, the calculation system 102 being constructed and arranged to carry out genomic calculations.

When the calculation system 102 is appealed by a user for carrying out a calculation requiring significant resources, the calculation system 102 can implement several calculation nodes. It is reminded that when a calculation node is assigned an action, this is actually made by a microprocessor of the calculation node controlled by instruction codes recorded in a memory of the calculation node. If an application is assigned an action, this is actually made by a microprocessor of the calculation node in a memory from which the instruction codes corresponding to the application are loaded.

To carry out these genomic calculations, the calculation system 102 is constructed and arranged to load computational biology tools enabling biomarker sequences to be organised and interpreted. In other words, by calculation, it is in particular meant organising and interpreting biomarker sequences. The computational biology tools that can be loaded by the calculation system 102 can for example be formed by different software types such as the software CRAC, the software CracTools, or even the software suite CRAC & the CT.

In a non-limiting implementation, the calculation system 102 can be constructed and arranged to classify short digital sequences of biological material. To do this, the calculation system 102 can for example implement the software called CRAC which is specialised in processing RNA-Seq sequences and enables the reads to be classified. The RNA-Seqs are obtained by high throughput sequencing of the RNAs.

In a non-limiting implementation, the calculation system 102 is further constructed and arranged to aggregate short digital sequences of biological material of a same class. To do this, the calculation system 102 can for example implement the software called CracTools which is specialised in post-processing the classified reads by means of the software CRAC and enables the reads of a same class to be aggregated to identify a biomarker sequence.

In another non-limiting implementation, the calculation system 102 is further constructed and arranged to identify a biomarker sequence answering a biological question. To do this, the calculation system 102 can for example implement the software suite called CRAC & the CT which connects the softwares CRAC and CracTools in order to identify biomarker sequences answering a precise biological question.

Further, each of the applicative nodes 101 includes a human-machine interface 103 constructed and arranged to communicate with the calculation system 102 of the applicative node 101. This human-machine interface 103 can be in the form of a SaaS type Web application. This Web application enables the user to be interfaced with a calculation system 102 enabling the biomarker sequences to be organised and interpreted but also a knowledge base to be consulted and edited.

In order to be able to consult and edit the knowledge base, the architecture 100 also includes an interface 104 for accessing a knowledge base 105, the interface 104 for accessing the knowledge base 105 is for example formed by an API REST.

The knowledge base 105 is constructed and arranged to communicate with the plurality of applicative nodes 101 by means of the access interfaces 104. The knowledge base 105 includes in particular genomic data.

Further, the knowledge base 105 includes a plurality of private spaces 106, each of the private spaces 106 being constructed and arranged:
- to contain metadata and results from a calculation carried out by the calculation system 102 of an authenticated entity including 1 to n user(s), and
- to be read and write only accessible to the users of the authenticated entity.

Each entity including one or more users thus has a private space 106 in which the resources (i.e. the results of calculations) are hidden to the other entities of the architecture 100 for the purpose of fulfilling the confidentiality need that some users would desire. It is thus not possible to the other users of other entities to consult them.

This private base 106 contains all the work data of the user or user(s) of an authenticated entity. To that end, data from the private space 106 are encrypted by the encryption key of the entity of the user. Thus, only the users of the entity can decrypt the content of their private space 106 in the knowledge base 105.

The knowledge base 105 also includes a plurality of shared spaces 107, each of the shared spaces 107 being constructed and arranged:
- to contain metadata and results from collaborative calculations carried out by the calculation systems 102, of an authenticated entity including 1 to n user(s), and
- to be read and write only accessible to the users of the authenticated entities and benefiting from a consultation right to said space.

Each entity thus has a shared space 107 for which it is possible to invite other users of one or more other entities in order to carry out a private but collaborative work. The shared space 107 contains all the common data within the scope of a collaborative project between several users of one or more other entities and thus allows data exchanges between users belonging to different entities but working on a same project.

In order to ensure security of the data stored, the data from a shared space 107 are stored being encrypted in the knowledge base 105. Consequently, the storage is only accessible from the calculation systems 102 authenticated to this shared space 107.

In one implementation, the user encrypts himself/herself his/her data in the (common) knowledge base via the human-machine interface used. In this case, the security is increased by the fact that only he/she has access to his/her encryption key and thus only he/she is technically capable of reading the encrypted data.

The knowledge base 105 also includes a common space 108, the common space 108 being accessible to all the users of the authenticated entities of the architecture 100.

In other words, the knowledge base 105 includes a public base 108 which contains all the public data accessible by all the users recorded in the architecture 100. It should be highlighted that any third party not authenticated to the architecture 100 has no access to this common space 108, nor even indeed to the architecture 100.

As a result, the architecture 100 offers the possibility to the users to gather data in a private space 106 (creation of a group by affinity), into a shared space 107 (creation of a group with a higher size by affinity) or into a common space 108. A space 106, 107 or 108 makes up a set of data gathered according to one or more criteria.

A space 106, 107 or 108 can make up, for example, a set of data gathered according to a (private, shared or common) confidentiality and property (the group of users that inserted these data) criterion.

Further, a user belonging to an entity can, at any time, move by means of his/her human-machine interface 103 his/her data from one space to another within the knowledge base 105. Thus, he/she has the entire control of his/her data and can share them, at any time, with the network of users, of his/her choice. He/she can only modify the confidentiality criterion, not the property criterion.

For example, a user A shares some of his/her data such that they are accessible to a user B. Then, he/she moves his/her data from his/her private space 106 to a shared space 107 of his/her entity by using his/her decryption key, and then he/she associates a read right to this shared space 107 with the user B. The latter can thus consult the biomarker sequences present in the shared base 107 of the user A.

According to another example, a user C shares some of his/her data such that they are accessible to all the users recorded in the architecture 100. Then, he/she moves his/her data from his/her private space 106, by means of his/her human-machine interface 103, to the common space 108 by using his/her decryption key. All the users authenticated to the architecture 100 have thereby access to the decrypted data.

In a non-limiting implementation, the biomarker sequences of the knowledge base are all associated with key words. If a user works on a particular type of data, he/she can share his/her work by using the associated key words. In this case, the other users working on this particular type of data will be immediately informed about it, and the association is either common, or private.

On the other hand, as already discussed, as soon as a calculation made by a user via at least one calculation system 102 is ended, the results are transmitted to the knowledge base 105 via an access interface 104 which enables the software code to be connected to the knowledge base 105, for example via an API REST type interface. The result of each calculation corresponds to a list of biomarker sequences of a different type as a function of the computational biology software implemented.

The human-machine interface 103 enables the user to submit NGS data files and to interface the user with a calculation system 102 enabling the biomarker sequences to be organised and interpreted, but also the knowledge base 105 to be consulted and edited.

This knowledge base 105 is thus capable of storing information of different types, of connecting all these information to each other and of associating metadata with biomarker sequences, and then of sharing them among several users with a security level defined beforehand.

In other words, this knowledge base 105 includes public data and is continuously supplied with the calculations (or analyses) of the users, and then corrected and updated. Indeed, each user can both consolidate his/her results with respect to all the biomarkers he/she will have identified, and then achieve in turn the content of the knowledge base by associating new metadata with biomarkers.

For example, a clinician can exchange, for each patient or clinical protocol, his/her information and interpretations with other centres (e.g. network between several university hospital centres), which will enable him/her in turn to enrich data on the patient's pathology, better understand and take the treatment in charge, and thus to be able to integrate information listed in the knowledge base 105.

This modular architecture 100 offers flexibility making it possible to be readily integrated to future medical tools which will enable the range of offers to be readily completed with new applications but also to guarantee the most precise results of the market. This type of architecture 100 enables the user to directly access the applications via the human-machine interface 103 and to consult or download his/her results interpreted on line.

In a non-limiting implementation, the architecture 100 includes a set of resources 109 enabling the biomarker sequences present in the knowledge base 105 to be organised.

These resources are all implemented within the knowledge base 105.

For example, the architecture 100 includes a system for identifying an entity and elements it handles (for example reads). As previously discussed, an entity is formed by a pool of users and elements they handle. Consequently, the entity can designate one or more users but can also identify a service of the user(s) (in the latter case, this service is totally independent of other services of the same user).

For example, an analysis has its own identifier but also property (user and entity) and confidentiality (shared or private common space) information.

The architecture 100 can also include a system for identifying and authenticating a user. Consequently, the system for identifying and authenticating a user represents a user of the architecture, for example a researcher or even a clinician. In other words, a person which creates and consults data from a high throughput sequencing, is in no way a patient who has been analysed. The user is identified with a single name (the login) and is authenticated with a password that only he/she knows. The system identifies the user if said user exists in the identification database. The system uses a "digest" (checksum of the password) of the authentication data to perform a comparison and validate the authentication. The identification database contains for each user the encryption key of the entity to which he/she is attached. This key is itself encrypted with the password of the user. During the authentication, the system thus uses the password of the user to release the encryption key of the entity. This key is then encrypted with an asymmetric system before being sent to the user. With this architecture, these security functionalities are obtained:

the passwords are not stored,
the encryption keys are only accessible with a valid password of a permitted user,
the user can not consult his/her own encryption key,
the user carries with him/her a certificate ensuring he/she has been properly identified and authenticated.

The architecture 100 can also include a system for identifying a calculation associated with at least one user and one entity. In other words, this system enables the results of an analysis uniquely associated with a user who is the initiator of the analysis as well as with the entity related to the initiator of the analysis to be designated. For example, the system for identifying a calculation associated with at least one user and one entity can contain information obtained with the software suite CRAC & the CT. The resulting data can be used for detecting biomarker sequences and feed the knowledge base.

The architecture 100 can also include a system enabling the obtained results to be correlated.

For example, if an analysis generates a biologically erroneous biomarker, it is possible to search for the analyses that had the same previous result and thus to avoid useless biological tests.

The architecture 100 can also include a system for logically gathering identifiers of calculations associated with one user and one entity. This gathering system enables the understanding of a biological problem, a patient prognostic or diagnostic to be improved since it makes it possible to have an overview of the calculations (e.g. the biomarker sequences) which are correlated with each other by applying a defined rule.

For example, it is possible to gather the analyses from patients having a same pathology to determine common points or statistic information therefrom.

The architecture 100 can also include a system enabling a piece of meta-information to be associated with data from the knowledge base. This system can be used by the users for the purpose of associating a text message discussing the result of a calculation. For example, it is possible to generate an inter-entity discussion on an issue identified by an analysis group or a specific marker. This discussion allows a rapid exchange among the different specialists on precise questions.

In a non-limiting implementation, the knowledge base 105 is formed by a database ring.

In other words, data storage relies on a knowledge base of the key/column type database ring. Thus, all the users access in real time the knowledge base in the read and write modes. The knowledge base consists of resources that can be added/deleted as a function of the capacity and performance need, thus enlarging the storage ring. This enables to benefit from a distributed, unlimited and highly available storage since data are replicated in three different places.

The location of these replications is automatically calculated according to (machine and geographical) criteria such that it covers all possible failures. For example, a piece of data A is stored on a machine X with two other copies on machines Y and Z. All the machines X, Y and Z make up the entire knowledge base.

It is reminded that when the knowledge base is assigned an action, this is actually carried out by a microprocessor of the knowledge base controlled by instruction codes recorded in a memory of the knowledge base. If an application is assigned an action, this is actually performed by a microprocessor of the knowledge base in a memory from which the instruction codes corresponding to the application are recorded.

Generally, in a conventional database, there is the "CAP" theorem: C for "Consistency", A for "Availability" and P for "Partition". According to the invention, the knowledge base is based on A to always guarantee an answer and on P to allow a massive storage ("big data"). As regards C, it is optimum enough to fulfill consistency needs within the scope of the use. No current database can fulfill the three conditions (CAP). To the architecture according to the invention, a second C for "Confidentiality" is further added because it enables a security level higher than the existing standard that a conventional database could fulfill to be guaranteed.

Further, in the implementation of the architecture according to the invention, for each analysis (or calculation), elements of the knowledge base (genomic biomarkers) are generated. Each of these elements contains a reference on the analysis analyses that have generated it. Hence, it is possible to gather the analyses sharing the same elements (biomarkers) and, by extrapolation, the users of the analyses can be contacted or can contact with each other.

The architecture according to the invention enables the analysis to be completely democratised such that a clinician or biologist is fully autonomous about his/her analysis (no more need of computational biology and biostatistic specialists between him/her and his/her NGS data), with a chosen security level, a defined share, a guaranteed quality, appropriate visual tools and a delimited share.

The invention claimed is:

1. A system for analysing genomic data, comprising:
a plurality of application nodes, each application node of the plurality of application nodes including one or more microprocessors and a non-transitory computer-readable storage medium comprising computer instructions stored and executable by the one or more microprocessors of the application node for:
forming a calculation system that carries out genomic calculations,
forming a human-machine interface constructed and arranged to enable a user of the system to communicate with the calculation system to instruct the calculation system to carry out the genomic calculations,
forming an interface for accessing a knowledge database,
the knowledge database including one or more microprocessors and a non-transitory computer-readable storage medium comprising computer instructions stored and executable by the one or more microprocessors of the knowledge database for communicating with the plurality of application nodes, said knowledge database comprising a non-transitory storage system containing said genomic data, the non-transitory storage system comprising
a plurality of private spaces assigned to a corresponding plurality of authenticated entities such that each private space of the plurality of private spaces is accessible by a corresponding one authenticated entity of the plurality of authenticated entities, each authenticated entity of the plurality of authenticated entities being an entity that has been authenticated by the system and each authenticated entity including 1 to n user(s), said private space accessible by said corresponding one authenticated entity being constructed and arranged:
- to contain metadata and results from genomic calculations carried out for the 1 to n user(s) of said corresponding one authenticated entity, and
- to be read-only accessible to each of the 1 to n user(s) of the corresponding one authenticated entity such that the metadata and results from genomic calculations carried out for the 1 to n user(s) of said corresponding one authenticated entity are accessible to each user of the 1 to n user(s).

2. The system for analysing genomic data according to claim 1, wherein the non-transitory storage system of the knowledge database further comprises a plurality of shared spaces, each of the shared spaces being constructed and arranged:
- to contain metadata and results from genomic calculations carried out for the 1 to n user(s) of said corresponding one authenticated entity and for the 1 to n user(s) of at least another one authenticated entity of said plurality of authenticated entities, and
- to be read-only accessible to each of the 1 to n user(s) of the corresponding one authenticated entity and to each of the 1 to n user(s) of the at least another one authenticated entity of said plurality of authenticated entities, the 1 to n user(s) of the at least another one authenticated entity of said plurality of authenticated entities benefiting from a consultation right to said shared space.

3. The system for analysing genomic data according to claim 1, wherein the non-transitory storage system of the knowledge database further comprises a common space, said common space being accessible to all the users of the authenticated entities of the system.

4. The system according to claim 1, wherein the calculation system is constructed and arranged to classify digital sequences of biological material comprising only several hundred of nucleotides.

5. The system according to claim 4, wherein the calculation system is constructed and arranged to aggregate the digital sequences of biological material of a same class.

6. The system according to claim 1, wherein the calculation system is constructed and arranged to identify a biomarker sequence answering a biological question.

7. The system according to claim 1, further comprising a non-transitory computer-readable storage medium comprising computer instructions stored and executable by a microprocessor to:
- identify the entity and elements it handles,
- identify the 1 to n user(s) of the entity,
- identify a calculation associated with at least one user of the 1 to n user(s) of the entity,
- enable calculations carried out to be correlated,
- gather identifiers of calculations associated with a user of the 1 to n user(s),
- enable a piece of meta-information to be associated with data from the knowledge database.

8. The system according to claim 1, wherein the knowledge database is configured as a ring database.

* * * * *